(12) United States Patent
Qiu

(10) Patent No.: US 9,132,248 B2
(45) Date of Patent: Sep. 15, 2015

(54) SUCTION-TYPE PORTABLE ATOMIZER

(75) Inventor: Weihua Qiu, Jiangsu (CN)

(73) Assignee: JOYETECH (CHANGZHOU) ELECTRONICS CO., LTD., Jiangsu (CN)

( * ) Notice: Subject to any disclaimer, the term of this patent is extended or adjusted under 35 U.S.C. 154(b) by 334 days.

(21) Appl. No.: 13/424,712

(22) Filed: Mar. 20, 2012

(65) Prior Publication Data

US 2012/0199663 A1    Aug. 9, 2012

Related U.S. Application Data

(63) Continuation of application No. PCT/CN2011/077010, filed on Jul. 9, 2011.

(30) Foreign Application Priority Data

Nov. 1, 2010    (CN) .......................... 2010 1 0527480

(51) Int. Cl.
*A61M 15/00* (2006.01)
*A61M 15/06* (2006.01)
(Continued)

(52) U.S. Cl.
CPC .............. *A61M 15/06* (2013.01); *A24F 47/008* (2013.01); *A61M 11/041* (2013.01); *A61M 11/042* (2014.02); *A61M 15/0081* (2014.02); *A61M 2205/276* (2013.01); *A61M 2205/70* (2013.01)

(58) Field of Classification Search
CPC ... A24F 47/002; A24F 47/004; A24F 47/008; A62M 15/06; A62M 15/0081; A62M 11/041; A62M 11/042; A62M 2205/70; A62M 2205/276

USPC ............ 128/200.14, 202.21, 202.22, 203.26, 128/203.21, 203.27, 203.12, 203.15, 128/203.17; 131/194, 271, 273
See application file for complete search history.

(56) References Cited

U.S. PATENT DOCUMENTS 4,338,931 A * 7/1982 Cavazza ................... 128/203.15
6,490,487 B1 * 12/2002 Kraus et al. ..................... 607/60
(Continued)

FOREIGN PATENT DOCUMENTS

| CN | 2889333 Y | 4/2007 |
|---|---|---|
| CN | 201067728 Y | 6/2008 |

(Continued)

OTHER PUBLICATIONS

International Search Report (Form PCT/ISA210) of the corresponding international application No. PCT/CN2011/077010, dated Oct. 20, 2011.
The extended European Search Report of corresponding European Application No. 11837468.5, dated Jul. 26, 2013.

*Primary Examiner* — Justine Yu
*Assistant Examiner* — Douglas Sul
(74) *Attorney, Agent, or Firm* — J.C. Patents

(57) ABSTRACT

The present invention relates to a portable atomizer. The portable atomizer includes a casing, a liquid storage case, an atomizing device and a power supply. The atomizing device further includes a liquid guiding assembly which includes a second suction nozzle and a liquid guiding rope; one end of the second suction nozzle is inserted into the storage cavity of the liquid storage case; the other end of the second suction nozzle intercommunicates with the atomizing cavity of the suction nozzle holder; a part of the liquid guiding rope is surrounded by the heater, and two ends of the liquid guiding rope are guided into the second suction nozzle. The present invention enables to guide the stored medicinal liquid uniformly onto the heater, providing an easy access to fresh medicinal liquid for a user.

11 Claims, 4 Drawing Sheets

(51) Int. Cl.
*A24F 47/00* (2006.01)
*A61M 11/04* (2006.01)

(56) References Cited

U.S. PATENT DOCUMENTS

| | | | | |
|---|---|---|---|---|
| 6,557,551 | B2 * | 5/2003 | Nitta | 128/203.17 |
| 6,557,552 | B1 * | 5/2003 | Cox et al. | 128/203.27 |
| 7,131,599 | B2 * | 11/2006 | Katase | 239/102.1 |
| 8,375,957 | B2 * | 2/2013 | Hon | 131/194 |
| 2001/0020470 | A1 | 9/2001 | Zupan | 128/200.24 |
| 2003/0033055 | A1 | 2/2003 | McRae et al. | 700/266 |
| 2006/0032501 | A1 | 2/2006 | Hale et al. | 128/203.12 |
| 2008/0110454 | A1 | 5/2008 | White et al. | 128/200.23 |
| 2009/0272379 | A1 * | 11/2009 | Thorens et al. | 128/202.21 |
| 2011/0005535 | A1 * | 1/2011 | Xiu | 131/273 |
| 2011/0011396 | A1 * | 1/2011 | Fang | 128/202.21 |
| 2011/0226236 | A1 * | 9/2011 | Buchberger | 128/200.23 |
| 2013/0213419 | A1 * | 8/2013 | Tucker et al. | 131/328 |

FOREIGN PATENT DOCUMENTS

| | | |
|---|---|---|
| CN | 201213951 Y | 4/2009 |
| CN | 101731750 A | 6/2010 |
| CN | 201491721 U | 6/2010 |
| CN | 201878765 U | 6/2011 |
| EP | 0 057 243 A1 | 8/1982 |
| EP | 0 430 559 A2 | 6/1991 |
| GB | 2 466 758 | 7/2010 |
| WO | WO03/034847 A1 | 5/2003 |

* cited by examiner

SUCTION-TYPE PORTABLE ATOMIZER

CROSS-REFERENCE TO RELATED APPLICATIONS

This application is a continuation of International Application No. PCT/CN2011/077010, filed on Jul. 9, 2011, which claims the priority benefit of China Patent Application No. 201010527480.9, filed on Nov. 1, 2010. The contents of the above identified applications are incorporated herein by reference in their entirety.

FIELD OF THE TECHNOLOGY

The present invention relates to an atomizing device, and more particularly to a suction-type portable atomizer

BACKGROUND

Coupling with increasing interaction among the general public and their social activities, many people are haunted by problems such as bad breath; although chewing gum and throat tablets, etc, could address the problems, their wastes such as chewed gum and wrapping tinfoil may lead to environmental pollution.

According to a previous proposal, the medicinal liquid could be heated mechanically for the users; although the users are accustomed to such method, unstable property of traditional mechanical structure likely causes damage and difficulty in operation. So, an ultrasonic atomizer was launched with the technical progress. Unlike a mechanical device that enables liquid atomizing by heating, the ultrasonic atomizer could generate atomizing droplets based on oscillatory excitation of ultrasonic wave for the liquid under specific frequency and feed into the human mouth where a smoking feeling is produced. Such atomizing scheme resembles the common household ultrasonic heater, but the atomizing capacity of the ultrasonic atomizer is relatively small, and the energy isn't fully utilized.

Some currently available atomizers have the following shortcomings: firstly, the medicinal liquid is injected into the filling layer in the suction nozzle chamber, so the medicinal liquid is not fresh enough; and the storage capacity is small, so when the medicinal liquid is used up, the medicinal liquid must be dripped into the atomizer more frequently by the user to continue using it; in such case, the users have to carry a bottle of medicinal liquid along with themselves in their outdoor activities or when going to work and have to drip the medicinal liquid by themselves; secondly, the atomizers currently available are generally screwed, so the users have to screw up the fuel cell with more efforts, making it aesthetically unpleasing and unsanitary; thirdly, when the atomizer is used, the medicinal liquid stored in the filling layer couldn't be uniformly fed to the heater, namely, droplets with very small diameter couldn't be formed during heating, and droplets with big diameter couldn't be fed into the human mouth in tune with the negative pressure of the mouth, nor heated since they are dripped out of the heater under the function of gravity force.

SUMMARY

The major purpose of the present invention is to provide a suction-type portable atomizer, which enables to guide the stored medicinal liquid uniformly onto the heater, providing an easy access to fresh medicinal liquid for the users.

To this purpose, the technical scheme of the present invention is as follows:

A suction-type portable atomizer, a suction nozzle is disposed at one end of a casing; and a liquid storage case with a storage cavity is disposed within the casing; one end of the liquid storage case is connected with an atomizing device which is connected with a power supply; the power supply comprises a housing and a fuel cell, a control circuit and a contact probe disposed in the housing; an output end of the control circuit is connected with the contact probe which is plugged into the contact conductor; the atomizing device comprises an atomizing assembly including a suction nozzle holder and a heater; one end of the suction nozzle holder is provided with an atomizing cavity, and the other end of the suction nozzle holder is provided with an air vent intercommunicated with the atomizing cavity; the heater is fixed into the atomizing cavity.

The atomizing device further comprises a liquid guiding assembly including a suction nozzle and a liquid guiding rope; one end of the suction nozzle is inserted into the storage cavity of the liquid storage case, such that liquid seal is formed at a contact part of the suction nozzle and liquid storage case; the other end of the suction nozzle is intercommunicated with the atomizing cavity of the suction nozzle holder; the liquid guiding rope is wound onto the heater, and two ends of the liquid guiding rope are guided into the suction nozzle.

With the aforementioned scheme, there isn't any filler in the liquid storage case, so the medicinal liquid is very fresh. Since two ends of the liquid guiding rope are guided into the suction nozzle, so the medicinal liquid in the liquid storage case could be sealed by the liquid guiding rope, such that the medicinal liquid will not flow into the atomizing cavity along the suction nozzle under the gravity force; moreover, the medicinal liquid in the liquid storage case can be guided onto the heater under negative pressure; since the liquid guiding rope is wound onto the heater, the medicinal liquid could be uniformly fed to the heater, namely, small droplets could be formed during heating with almost no big droplet produced so that all the medicinal liquid which is sucked out could be heated and sprayed into the human mouth within a normal range of negative pressure.

With use of the liquid guiding sleeve, when the medicinal liquid is sucked under bigger negative pressure, a portion of medicinal liquid will not be heated, but flow along with negative-pressure air stream. In the flow process, the medicinal liquid will fall down onto the liquid guiding sleeve under the gravity force, or otherwise the medicinal liquid isn't fully heated by the heater, leading to excessive big droplets contained in the vapour; with the flow of negative-pressure air stream, these big droplets will also fall down onto the liquid guiding sleeve under the gravity force, where the medicinal liquid not yet heated will be adsorbed, then fed close to the heater in the atomizing cavity through the liquid guiding sleeve and liquid guiding hole, and atomized by the heater. Hence, the medicinal liquid could be recycled by the liquid guiding sleeve, and then guided to the heater. Moreover, with use of the liquid guiding sleeve, the medicinal liquid is heated and atomized under gravity force without need of manual efforts to recycle the medicinal liquid with negative pressure for heating and atomizing.

The other purpose of the present invention is to provide a control circuit and a control method for the atomizer by the following technical scheme, so as to prevent the keying switching from being turned on by maloperation:

A control circuit for the atomizer, the control circuit comprises a keying switch adapted to send out a signal for turning on or turning off the control circuit.

The control circuit also comprises a single chip microprocessor with locking function connected with the keying switch, which is locked without signal output or unlocked after receiving a signal from the keying switch.

The control circuit also comprises a transistor connected with an output end of single chip microprocessor for signal amplification.

A method for controlling the atomizer, which including the following steps:

Step (1), initializing a system, in which a single chip microprocessor configures a locking time and an unlocking time of a circuit;

Step (2), the single chip microprocessor detecting a signal output from a keying switch, in which, when the single chip microprocessor in a locked state receives Y-times switching signals from the keying switch within Q seconds, the single chip microprocessor is unlocked; next, when the single chip microprocessor receives a signal from the keying switch once more, the circuit is turned on and the single chip microprocessor outputs an electrical signal to a transistor;

Step (3), the transistor amplifying the signal from the single chip microprocessor and then supplying power to a load; if the atomizer is not to be used, when the single chip microprocessor receives X-times switching signals from the keying switch within P seconds, the single chip microprocessor is locked without signal output.

Based on the above scheme, as the circuit is normally turned on by unlocking with the keying switch, the circuit could be locked by the single chip microprocessor to avoid accident with improved safety even in the case of maloperation by the users.

In the attached figures, 10: casing; 11: front cover of suction nozzle; 12: rear cover of suction nozzle; 20: liquid storage case; 21: casing body; 22: casing cover; 23: liquid isolating membrane; 24: air stream channel; 30: atomizing device; 310: suction nozzle holder; 311: heater; 312: sleeving; 313: atomizing cavity; 314: air vent; 315: liquid guiding hole; 320: liquid guiding rope; 321: liquid guiding sleeve; 322: liquid guiding pipe; 323: base body; 330: main body of atomizer; 331: contact conductor; 332: base of contact conductor; 333: air inlet; 41: housing; 42: fuel cell; 43: control circuit; 44: contact probe.

DETAILED DESCRIPTION

Figure 1:
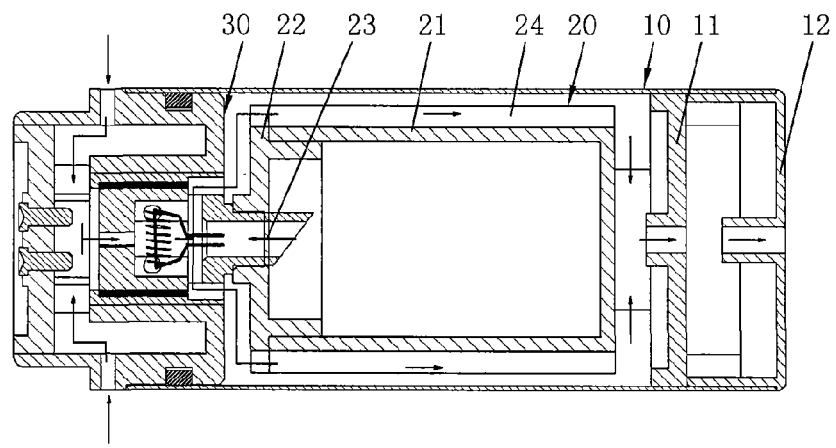
FIG. 1 is a structural view of the atomizer according to an embodiment of the present invention.
Figure 2:
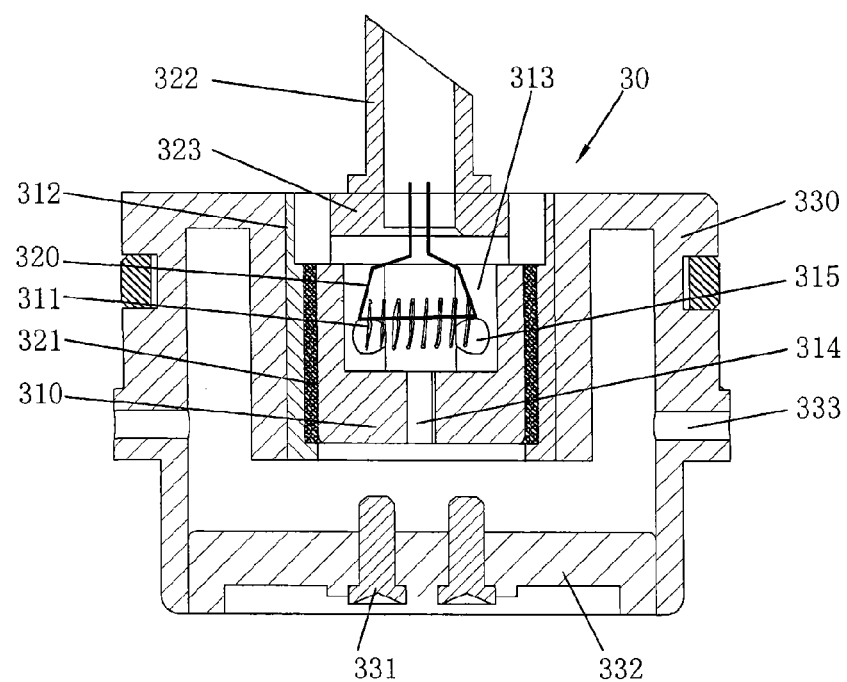
FIG. 2 is a structural view of the atomizing device according to an embodiment of the present invention.
Figure 3:
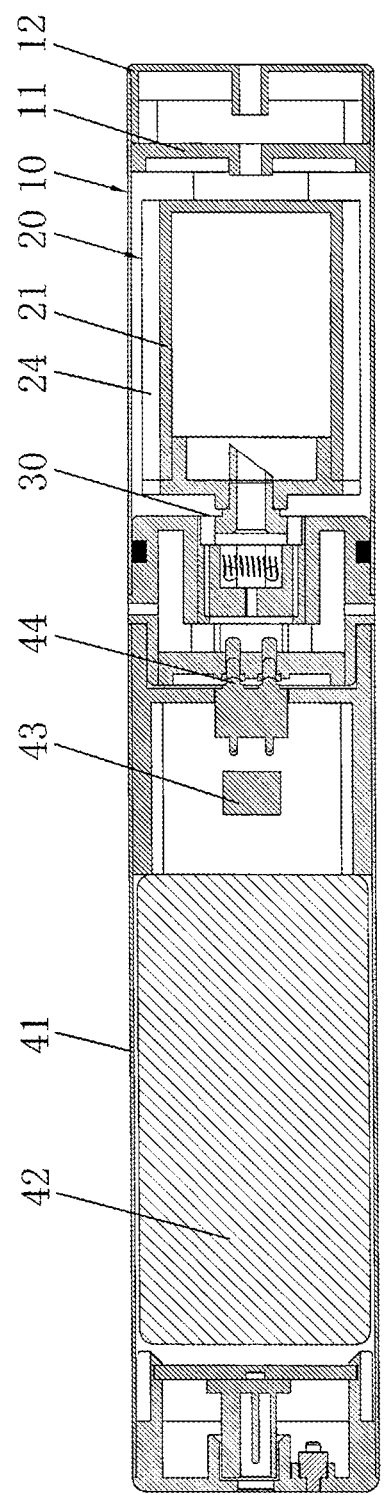
FIG. 3 is an assembly view of the atomizer and power supply according to an embodiment of the present invention.

The present invention hereto is further described with reference to the following drawings and preferred embodiments:

FIGS. 1-3 depict a suction-type portable atomizer according to an embodiment of the present invention. After the atomizer of the present invention is connected with the power supply, the stored medicinal liquid is heated and atomized, then fed into the human mouth; the medicinal liquid may be a health-related type, an odour-removing type, or other kinds of medicinal liquids useful to human health. The atomizer according to an embodiment of the present invention mainly comprises a casing 10, a liquid storage case 20 and an atomizing device 30. The structures and functions of the suction-type portable atomizer according to embodiments of the present invention are described in detail with reference to the drawings.

Referring to FIG. 1, the casing 10 can be made of metal or other suitable material such as plastics; the cross section of the casing 10 can be of elliptical, round, or rectangular shape, or other suitable shape. One end of the casing 10 is securely connected to the suction nozzle, for example, by way of insertion, or threading; the suction nozzle comprises a front cover 11 and a rear cover 12. Air vents are arranged onto both the front cover 11 and rear cover 12 of the suction nozzle; these air vents are used for transferring negative pressure produced by the human mouth, and feeding the atomized medicinal liquid into the human mouth.

Referring to FIG. 1, the liquid storage case 20 with a storage cavity is disposed within the casing 10, and used for storing medicinal liquid. The liquid storage case 20 has a casing body 21 and a casing cover 22 connected with the casing body 21; through-hole is set on the casing cover 22 for insertion of the suction nozzle; a liquid isolating membrane 23 that can be punctured through is disposed at the through-hole, such that a liquid seal is formed between the liquid isolating membrane 23 and suction nozzle after the liquid isolating membrane 23 is punctured through by the suction nozzle. No filling layer is disposed within the cavity of the liquid storage case, and the medicinal liquid is directly stored in the cavity, such that the users could enjoy fresh medicinal liquid without the need of storing it in the filling layer for a longer period. The cross section of the casing body 21 can be the same as that of the casing 10; the casing body 21 and casing 10 are mated by clearance fit or transition fit; if transition fit is introduced, an air stream channel 24 for transmitting air is disposed on the side wall of the liquid storage case 20.

Referring to FIGS. 1 and 2, one end of the liquid storage case 20 is connected with an atomizing device 30, so the medicinal liquid in the liquid storage case 20 will be output into the atomizing device 30 under negative pressure. The atomizing device comprises an atomizing assembly, a liquid guiding assembly and a connector assembly.

Referring to FIG. 2, the atomizing assembly includes a suction nozzle holder 310, a heater 311 and a sleeving 312. The suction nozzle holder 310 can be made of ceramics, one end of which is provided with an atomizing cavity 313; the other end of the suction nozzle holder 310 is provided with an air vents 314 intercommunicating with the atomizing cavity; the air vents 314 intecommunicate with atmosphere to form negative pressure during inhalation; when air vents intercommunicate with the atomizing cavity, negative pressure will be formed easily during inhalation of human mouth, such that the atomized medicinal liquid is fed into the human mouth. Liquid guiding holes 315 intercommunicating with the atomizing cavity are further disposed on the side wall of the suction nozzle holder; the aperture of the liquid guiding hole 315 on the external side wall of the suction nozzle holder is smaller than that on the internal side wall of the suction nozzle holder. The heater 311 is fixed into the atomizing cavity 313. In this preferred embodiment, the heater 311 generates heat energy through action of current, so it can be made of platinum wire or nickel chrome or Aludirome wire containing rare earth elements, and fabricated into tabular or circular shape. The sleeving 312 is sleeved onto external wall of the suction nozzle holder 310, helping to absorb a portion of heat from the suction nozzle holder 310, and reduce heat transfer from the suction nozzle holder 310 to the housing.

Referring to FIG. 2, the liquid guiding assembly includes a suction nozzle, a liquid guiding rope 320 and a liquid guiding sleeve 321. The suction nozzle has a liquid guiding pipe 322 and a base body 323; one end of the liquid guiding pipe 322 is connected with the base body 323, and the other end of the liquid guiding pipe 322 is a free end with an inclined or triangular end face. In this preferred embodiment, the free end is provided with an inclined face. Based on the inclined or triangular end face of the free end, this could help puncture easily the liquid isolating membrane 23 on the casing cover 22. A liquid seal is formed at the contact part of the suction nozzle and liquid storage case, namely: after puncturing the liquid isolating membrane 23 on the casing cover 22, the free end of the liquid guiding pipe 322 is inserted into the storage cavity of the casing body 21; as the liquid isolating membrane 23 is made of rubber, a liquid seal is thus formed at the contact part of the liquid guiding pipe and liquid isolating membrane 23. The other end of the suction nozzle intercommunicates with the atomizing cavity of the suction nozzle holder. Since the base body 323 is located over the atomizing cavity 313 or kept in contact with the atomizing cavity 313 (the atomizing cavity isn't blocked since the surface area of the base body is smaller than the area of the atomizing cavity 313), the base body could intercommunicate with the suction nozzle holder.

Referring to FIG. 2, as for the liquid guiding rope 320 in the liquid guiding assembly: the middle part of the liquid guiding rope 320 is wound onto the heater 311, and two ends of the liquid guiding rope 320 are guided into the suction nozzle, namely, two ends of the liquid guiding rope 320 are guided into the liquid guiding pipe 322. So, the medicinal liquid in the casing body 21 could be sealed by the liquid guiding rope, such that the medicinal liquid will not flow into the atomizing cavity 313 along the suction nozzle under the gravity force; moreover, the medicinal liquid in the casing body 21 is guided onto the heater under negative pressure. Since the liquid guiding rope is wound onto the heater, with the help of the liquid guiding rope, the medicinal liquid can be uniformly fed to the heater, namely, small droplets can be formed during heating with almost no big droplets produced so that all the medicinal liquid which is sucked out can be heated and sprayed into the human mouth within a normal range of negative pressure.

Referring to FIG. 2, as for the liquid guiding sleeve 321 in the liquid guiding assembly: the liquid guiding sleeve 321 capable of storing large-diameter suspended droplets is sleeved on the external wall of the suction nozzle holder, such that the liquid guiding sleeve 321 is located between the suction nozzle holder and the sleeving 312. The liquid guiding sleeve can be made of multi-layer foamed nickel screen. When the medicinal liquid is sucked out under quite big negative pressure, some of the medicinal liquid is not being heated, but flow along with negative-pressure air stream. In the flowing process, the medicinal liquid will fall down onto the liquid guiding sleeve 321 under the gravity force, or because the medicinal liquid isn't fully heated by the heater due to low heating temperature, leading to excessive big droplets contained in the vapour; with the flow of negative-pressure air stream, these big droplets will also fall down onto the liquid guiding sleeve 321 under the gravity force, the portion of medicinal liquid not being heated will be adsorbed by the liquid guiding sleeve, then fed to vicinity of the heater in the atomizing cavity through the liquid guiding sleeve and liquid guiding hole 315, and atomized by the heater. Hence, the medicinal liquid can be recycled by the liquid guiding sleeve 321, and then guided to the heater. Moreover, with the use of the liquid guiding sleeve 321, the medicinal liquid is heated and atomized under gravity force without need of manual efforts to recycle the medicinal liquid with negative pressure.

Referring to FIG. 2, as for the connector assembly of the atomizing device 30 fixed at the other end of the casing 10: the connector assembly includes a main body of atomizer 330, a contact conductor 331 wired with the heater 311 and a contact conductor base 332. A cavity for accommodating and retaining the atomizing assembly is formed at one end of the main body 330 in the casing; the sleeving 312 and other atomizing assembly elements are fixed in the cavity, and the sleeving 312 and the cavity are mated by interference fit. An air inlet 333 intercommunicating with the cavity is disposed on the side wall of the main body of atomizer for intecommunicating with atmosphere. The contact conductor base 332 is fixed at the other end of the main body exposed out of the casing 10, and the contact conductor 331 is fixed onto the contact conductor base 332; there are two contact conductors 331, each of which is connected separately with the anode and cathode of the power supply; every contact conductor is provided with an access hole for the contact probe. Additionally, a step is formed on the external surface of the main body of atomizer 330, and the main body of atomizer 330 is used for supporting the atomizing assembly and for connecting the power supply.

Referring to FIG. 3, a power supply is connected with one end of the main body of atomizer 330 exposed out of the casing 10; the power supply includes a housing 41 as well as a fuel cell 42, a control circuit 43 and a contact probe 44 disposed in the housing; one end of the housing 41 is reserved with a space for inserting the main body of atomizer 330; after the main body of atomizer 330 is inserted into the housing 41, the contact probe is inserted into the hole of the contact conductor. The control circuit is connected with the fuel cell, and the output end of the control circuit is connected with the contact probe.

Referring to FIG. 4, the control circuit includes a keying switch SW used to send out signals for turning on or off the control circuit; a single chip microprocessor IC1 with locking function connected with the keying switch, which is locked without signal output or unlocked after receiving signals from the keying switch; and a transistor Q1 connected with the output end of the single chip microprocessor for signal amplification. The control circuit also includes a detector Q2 for checking voltage of a fuel cell and whether an output is short circuited, and an LED D1 for indicating working state of the control circuit; the detector Q2 and LED D1 are respectively connected to the single chip microprocessor.

Atomizing process according to an embodiment of the present invention (the arrow in FIG. 1 indicates the flow direction of air stream and aerosol): a user connects the suction-type portable atomizer to the power supply, turns on the keying switch and releases the circuit locking, presses the keying switch again so that electric current flows through the contact conductor 331 to turn on the heater 311 in the atomizing assembly to heat up. Owing to the action of negative pressure, the medicinal liquid in the liquid storage case is guided onto the heater 311 through the suction nozzle and liquid guiding rope 320, where the medicinal liquid is atomized instantly under the high-temperature action of electrical heater 311. Aerosol formed by small suspended droplets in negative-pressure air stream flows into the front cover 11 of the suction nozzle through the air stream channel 24, then into the rear cover 12 of the suction nozzle, and finally into the user's mouth. After the medicinal liquid is used up, the suction nozzle could be unplugged if desired by the user, and then the medicinal liquid is added into the liquid storage case; alternatively, if the user does not want to continue using the medicinal liquid with a current flavor, a new liquid storage device could be used, and the old atomizer could be recycled or dismantled to avoid environmental pollution.

Figure 4:
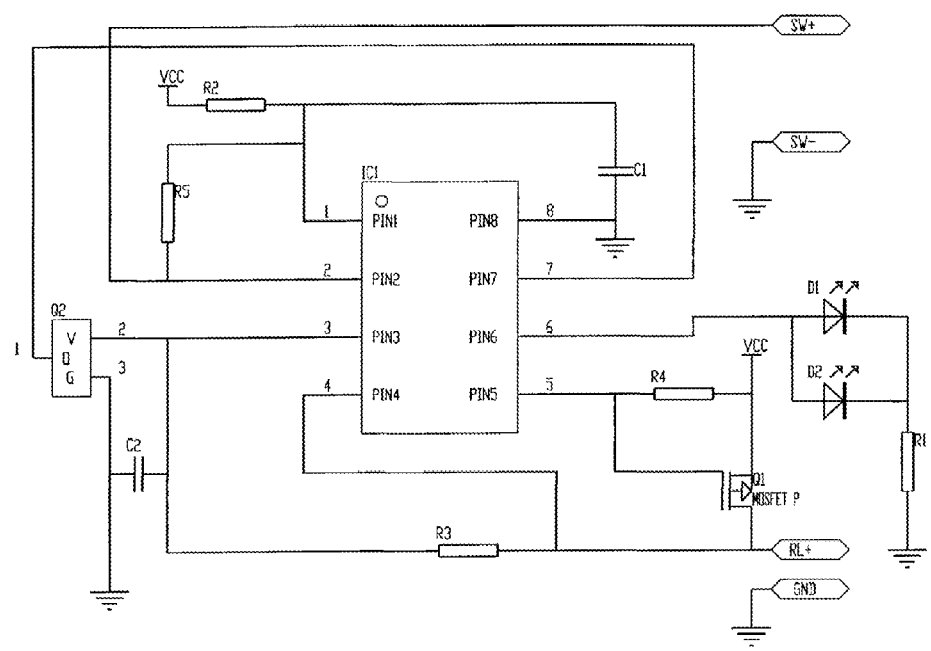
FIG. 4 is a schematic diagram of the control circuit according to an embodiment of the present invention.
Figure 5:
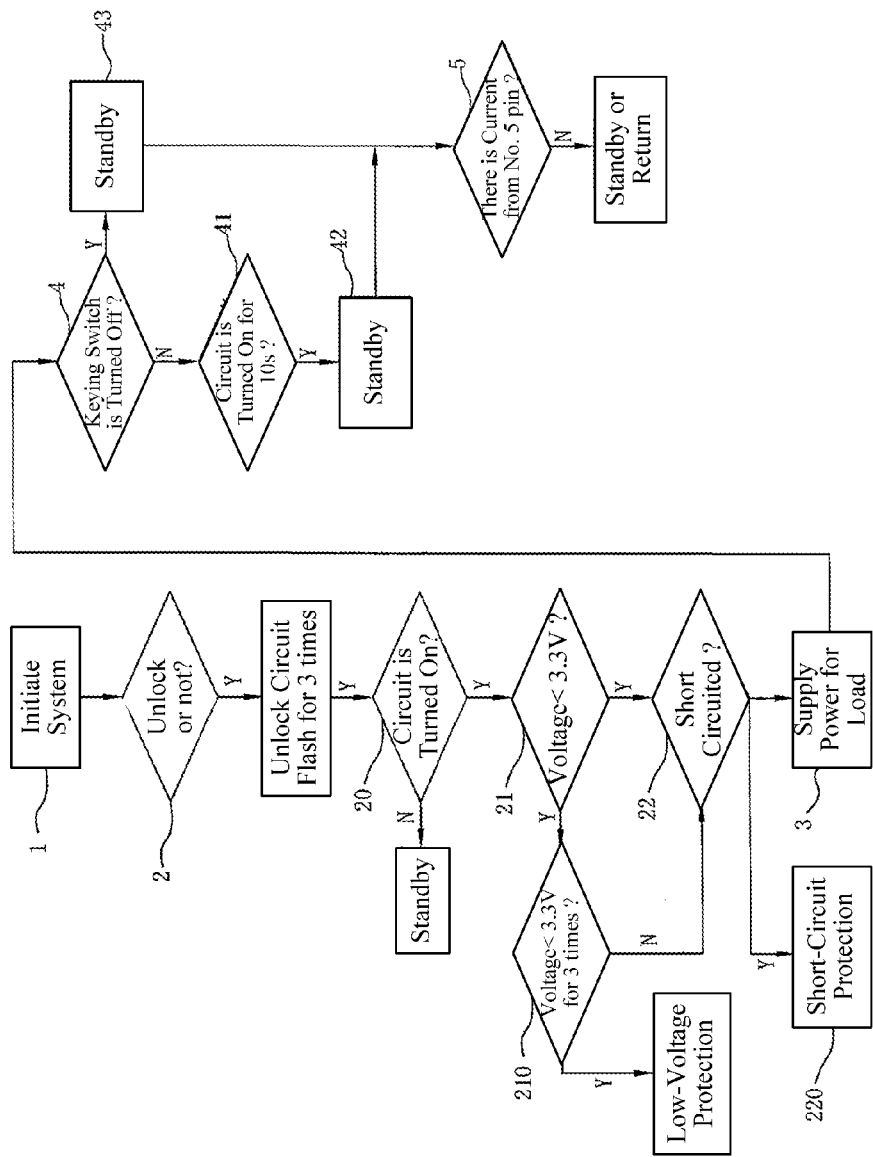
FIG. 5: a flow diagram of the control circuit according to an embodiment of the present invention.

Referring to FIGS. 4 and 5, the present invention also provides a special control circuit for the atomizer; the control circuit includes a keying switch SW adapted to send out signals for turning on or off the control circuit; a single chip microprocessor IC1 interlocked with the keying switch, which is locked without signal output or unlocked after receiving signals from the keying switch; and a transistor Q1 connected with the output end of the single chip microprocessor for signal amplification. The control circuit also includes a detector Q2 for checking voltage of a fuel cell and whether an output is short circuited, and an LED D1 for indicating working state of the control circuit; the detector Q1 and LED D1 are respectively connected to the single chip microprocessor.

The present invention also provides the following two preferred embodiments of methods for controlling the atomizer, which aims to prevent the keying switch from being accidentally touched to start the atomizer in daily life.

Preferred Embodiment I

This includes the following steps:

Step 1, initialize the system: the single chip microprocessor configures locking time and unlocking time of the circuit;

Step 2, the single chip microprocessor detects the output signals from the keying switch: when the single chip microprocessor in locked state receives 5-times switching signals from the keying switch within 1.5 seconds, the single chip microprocessor will be unlocked. Since the locking and unlocking is realized only when the keying switch is pressed for 5 times within 1.5 s, the single chip microprocessor would not be unlocked even if the switch is pressed for 1 or 2 times due to maloperation of the user. Besides, such configuration is very reliable owing to the fact that the keying switch couldn't be pressed for 5 times within 1.5 s arising from maloperation.

Next, after the circuit is unlocked, when the single chip microprocessor receives a signal from the keying switch once more, the circuit is turned on and the single chip microprocessor outputs electrical signals to the transistor.

Step 20, check if the circuit is turned on, namely: the single chip microprocessor judges whether the electrical level on No. 2 pin is low.

Step 21, if the checking result in Step 20 is true, the single chip microprocessor outputs the acquired voltage of the fuel cell to the detector Q2, which will judge if the voltage of the fuel cell is lower than 3.3V, and transmit the judgment result to the single chip microprocessor;

Step 210, if the judgment results in three consecutive times in Step 21 are true, the single chip microprocessor enters low-voltage protection state, and at the same time controls LED to flash for 40-times at 2 Hz;

Step 22, if the judgment result in Step 21 is false, the detector Q2 judges if the circuit is short circuited, and transmits the judgment result to the single chip microprocessor;

Step 220, if the judgment result in Step 22 is true, the single chip microprocessor enters short-circuit protection state, and controls LED to flash for 3 times at 3 Hz;

If the judgment result in Step 22 is false, the single chip microprocessor outputs signals to LED, such that LED is gradually highlighted to its maximum brightness within 0.6 s, meanwhile the electrical level of No. 5 pin of the single chip microprocessor becomes low, and the single chip microprocessor IC1 outputs signals to the transistor Q1;

Step 3, the transistor Q1 amplifies the signals from the single chip microprocessor and then power is supplied to the load; if the atomizer is not to be used, when the single chip microprocessor receives 5-times switching signals from the keying switch within 1.5 s, the single chip microprocessor enters a locked state without signal output. Locking the circuit could avoid turning on the circuit arising from maloperation, so the atomizer couldn't be started by maloperation to prevent the user from burning. If it's intended to use it continuously, enter into Step 4.

Step 4, during Step 3, the single chip microprocessor IC1 checks if the keying switch SW is turned off in real time;

Step 41, if the judgment result in Step 4 is false, the single chip microprocessor checks if the circuit is continuously turned on for 10 s; if the judgment result is false, it's required to return to step 4 for further checking;

Step 42, if the judgment result in Step 41 is true, LED is controlled to flash for 10 times, and then the single chip microprocessor enters a standby state;

Step 43, if the judgment result in Step 4 is true, the single chip microprocessor has no signal output to the transistor Q1, which is turned off and enters a standby state. Next, the user may choose to turn on the keying switch SW for turning on the circuit continuously; otherwise, the keying switch is turned on continuously for 5 times within 1.5 s, such that the circuit enters a locking state.

Step 5, the single chip microprocessor checks if there is current input from No. 5 pin; if true, it indicates that the fuel cell is charged by external power supply. In such case, No. 5 pin of the single chip microprocessor outputs a signal to turn on the transistor Q1 and charge the fuel cell; check every 6 s if there is current input until no current input occurs, then enter into a standby state, or return to Step 20.

Preferred Embodiment II

This preferred embodiment is implemented in the same way with the aforementioned one except for the difference with respect to locking and unlocking of the circuit.

The single chip microprocessor checks the output signals from the keying switch: the single chip microprocessor in a locked state could receive a first consecutive signal from the keying switch within 4 seconds, then the single chip microprocessor is unlocked; next, the single chip microprocessor receives a signal from the keying switch once more, and outputs an electrical signal to the transistor after the circuit is turned on. The transistor amplifies the signal from the single chip microprocessor and then output to the load; if the single chip microprocessor receives the second consecutive signal from the keying switch within 8 seconds, the single chip microprocessor is locked without signal output, namely, if pressing the keying switch for 8 s and making the keying switch continuously output a turn-off signal to the single chip microprocessor within this period, the single chip microprocessor could decide to lock the circuit.

What is claimed is:

1. A portable atomizer, comprising a casing, a liquid storage case, an atomizing device and a power supply, wherein a first suction nozzle is disposed at one end of the casing; and the liquid storage case is disposed within the casing and the liquid storage case has a storage cavity; one end of the liquid storage case is connected with the atomizing device which is connected with the power supply; the power supply comprises a housing and a fuel cell, a control circuit and a contact probe disposed in the housing; an output end of the control circuit is connected with the contact probe which is plugged into a contact conductor; the atomizing device comprises an atomizing assembly which includes a suction nozzle holder and a heater; one end of the suction nozzle holder is provided with an atomizing cavity, and the other end of the suction nozzle holder is provided with an air vent intercommunicating with the atomizing cavity; the heater is fixed into the atomizing cavity; characterized in that:

the atomizing device further comprises a liquid guiding assembly which includes a second suction nozzle and a liquid guiding rope; one end of the second suction nozzle is inserted into the storage cavity of the liquid storage case, such that liquid seal is formed at a contact part of the second suction nozzle and liquid storage case; the other end of the second suction nozzle intercommunicates with the atomizing cavity of the suction nozzle holder; a part of the liquid guiding rope is surrounded by the heater, and two ends of the liquid guiding rope are guided into the second suction nozzle;

the liquid guiding assembly further comprises a liquid guiding sleeve; the liquid guiding sleeve is sleeved on the suction nozzle holder; a liquid guiding hole intercommunicating with the atomizing cavity is disposed on a side wall of the suction nozzle holder; the atomizing assembly further comprises a sleeving disposed on the liquid guiding sleeve;

wherein medicinal liquid in the casing body is sealed by the liquid guiding rope, such that the medicinal liquid does not flow into the atomizing cavity along the second suction nozzle under gravity force, but is guided into the atomizing cavity via the liquid guiding rope under negative pressure; the liquid guiding sleeve is located downstream of the air vent of the suction nozzle holder in air flow direction, and configured such that large-diameter suspended droplets of the medicinal liquid which is sucked out of the liquid storage case and is not being heated or fully heated by the heater, fall down onto the liquid guiding sleeve under gravity force, the large-diameter suspended droplets are adsorbed by the liquid guiding sleeve and fed to vicinity of the heater in the atomizing cavity through the liquid guiding hole, and atomized by the heater.

2. The portable atomizer according to claim 1, wherein the liquid storage case comprises a casing body and a casing cover connected with the casing body; a through-hole is disposed on the casing cover for insertion of the second suction nozzle; a liquid isolating membrane is disposed at the through-hole and the liquid isolating membrane is puncturable, such that after the liquid isolating membrane is punctured through by the second suction nozzle, liquid seal is formed between the liquid isolating membrane and the second suction nozzle.

3. The portable atomizer according to claim 1, wherein the second suction nozzle comprises a liquid guiding pipe and a base body; one end of the liquid guiding pipe is connected with the base body, and the other end of the liquid guiding pipe is a free end with an inclined or triangular end face.

4. The portable atomizer according to claim 1, wherein the atomizing device further comprises a connector assembly fixed at one end different from the one end of the casing where the first suction nozzle is disposed; the connector assembly comprises a main body of the atomizer and a contact conductor wired with the heater; a containing cavity for accommodating and retaining the atomizing assembly is formed at one end of the main body of the atomizer in the casing; the contact conductor is fixed at the other end of the main body of the atomizer exposed out of the casing; an air inlet intercommunicated with the containing cavity is disposed on a side wall of the main body of the atomizer.

5. The portable atomizer according to claim 4, wherein the control circuit comprises:

a keying switch adapted to send out a signal for turning on or turning off the control circuit;

a single chip microprocessor with locking function connected with the keying switch, which is locked without signal output or unlocked after receiving a signal from the keying switch; and a transistor connected with an output end of the single chip microprocessor for signal amplification.

6. The portable atomizer according to claim 5, wherein the control circuit further comprises a detector for checking voltage of a fuel cell and whether an output is short circuited, and an LED for indicating working state of the control circuit; the detector and the LED are respectively connected with the single chip microprocessor.

7. A method for controlling the atomizer according to claim 1, characterized by comprising the following steps:

step (1), initializing a system, in which a single chip microprocessor configures a locking time and an unlocking time of a circuit;

step (2), the single chip microprocessor detecting a signal output from a keying switch, in which, when the single chip microprocessor in a locked state receives Y-times switching signals from the keying switch within Q seconds, the single chip microprocessor is unlocked; next, when the single chip microprocessor receives a signal from the keying switch once more, the circuit is turned on and the single chip microprocessor outputs an electrical signal to a transistor; and step (3), the transistor amplifying the signal from the single chip microprocessor and then supplying power to a load; if the atomizer is not to be used, when the single chip microprocessor receives X-times switching signals from the keying switch within P seconds, the single chip microprocessor is locked without signal output.

8. The method according to claim 7, characterized in that the atomizer is further provided with a detector and an LED respectively connected with the single chip microprocessor and conducts the following steps:

step (20), checking whether the circuit is turned on;

step (21), if a checking result in step (20) is true, the single chip microprocessor outputting an acquired voltage of the fuel cell to the detector, the detector judging whether the voltage of the fuel cell is lower than 3.3V and transmitting a judgment result to the single chip microprocessor;

step (210), if the judgment results in three consecutive times in step (21) are true, the single chip microprocessor enters low-voltage protection state, and at the same time controls LED to flash for 40-times.

9. The method according to claim 8, characterized in that:

step (22), if the judgment result in step (21) is false, the detector judges if the circuit is short circuited, and transmits a judgment result to the single chip microprocessor;

step (220), if the judgment result in step (22) is true, the single chip microprocessor enters short-circuit protection state, and at the same time controls LED to flash for 3 times; if the judgment result is false, the single chip microprocessor outputs a signal to LED, such that LED is highlighted gradually, meanwhile power is supplied to the load in step (3).

10. The method according to claim 9, characterized in that:

step (4), the single chip microprocessor checks if the keying switch is turned off;

step (41), if the judgment result in step (4) is false, the single chip microprocessor checks if the circuit is continuously turned on for 10 s; if a judgment result is false, it's required to return to step (4) for further checking;

step (42), if the judgment result in step (41) is true, LED is controlled to flash for 10 times, and then the single chip microprocessor enters a standby state;

step (43), if the judgment result in step (4) is true, the single chip microprocessor enters the standby state without signal output to the transistor.

11. The method according to claim 7, characterized by comprising the following steps:

step (1), initializing a system, in which a single chip microprocessor configures a locking time and an unlocking time of a circuit;

step (2), the single chip microprocessor detecting a signal output from a keying switch, in which, when the single chip microprocessor in a locked state receives a first consecutive signal output from the keying switch within N seconds, the single chip microprocessor is unlocked; next, when the single chip microprocessor receives a signal from the keying switch once more, the circuit is turned on and the single chip microprocessor outputs an electrical signal to a transistor; and step (3), the transistor amplifying the signal from the single chip microprocessor and then output an amplified signal to a load; if the atomizer is not to be used, when the single chip microprocessor receives a second consecutive signal from the keying switch within M seconds, the single chip microprocessor is locked without signal output.

* * * * *